(12) United States Patent
Lei et al.

(10) Patent No.: US 8,299,011 B2
(45) Date of Patent: Oct. 30, 2012

(54) ENCAPSULATED ACTIVE MATERIALS

(75) Inventors: Yabin Lei, Holmdel, NJ (US); Lewis Michael Popplewell, Morganville, NJ (US); Carol A. Joyce, Toms River, NJ (US); Xihua Lu, Holmdel, NJ (US); Jeffrey James McElwee, Toms River, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 259 days.

(21) Appl. No.: 12/562,578

(22) Filed: Sep. 18, 2009

(65) Prior Publication Data

US 2011/0071064 A1    Mar. 24, 2011

(51) Int. Cl.
*C11D 3/50*    (2006.01)
(52) U.S. Cl. .................................................. 510/438
(58) Field of Classification Search .................. 510/438
See application file for complete search history.

(56) References Cited

U.S. PATENT DOCUMENTS

| 4,280,833 A | 7/1981 | Beestman et al. |
| 5,925,595 A | 7/1999 | Seitz et al. |
| 2007/0042182 A1 | 2/2007 | Markus et al. |
| 2008/0200363 A1* | 8/2008 | Smets et al. ................. 510/475 |
| 2010/0119679 A1* | 5/2010 | Dihora et al. ................. 426/534 |

FOREIGN PATENT DOCUMENTS

| CH | WO2006006003 | 1/2006 |
| IL | WO2004098767 | 11/2004 |
| NL | 1693104 A1 | 8/2006 |

* cited by examiner

*Primary Examiner* — John Hardee
(74) *Attorney, Agent, or Firm* — Elizabeth M. Quirk; XuFan Tseng; Joseph F. Leightner

(57) ABSTRACT

The invention relates to products for washing and cleaning and/or care and protection of animate or inanimate surfaces that comprise micro-encapsulated benefit agents. The invention also relates to polyurethane and polyurea microcapsules.

2 Claims, No Drawings

ENCAPSULATED ACTIVE MATERIALS

FIELD OF THE INVENTION

The present invention relates to active materials that are encapsulated with a polyurea and polyurethane to form microcapsules compositions. The microcapsule composition is well suited for applications associated with laundry, personal care and cleaning products.

BACKGROUND OF THE INVENTION

Micro-encapsulation is used in a large variety of different applications where a compound needs to be delivered or applied to a target area while prior to delivery the compound needs to be protected from its environment, or where that compound needs to be released in a time-delayed way or only after a treatment has been applied that triggers release. Various techniques for preparing microcapsules are known in the art and are used, depending on the contents to be encapsulated, the environment wherein the microcapsules should retain their integrity and the desired release mechanism.

Interfacial polycondensation is a well-known technique for preparing microcapsules and versatile microcapsule wall materials that can be produced are polyureas and polyurethanes. Such wall materials are produced by having a first phase which is water-immiscible and comprises a polyfunctional isocyanate, i.e. a diisocyanate and/or a polyisocyanate, and a second aqueous phase which may comprise a polyfunctional alcohol or amine, i.e. a diol and/or polyol for obtaining a polyurethane capsule wall or a diamine and/or polyamine comprising —$NH_2$ and/or —NH groups for obtaining a polyurea capsule wall.

If the material to be encapsulated is hydrophobic it will be included in the water-immiscible phase, whereafter the two phases are mixed by high shear mixing to form an oil-in-water emulsion. In this emulsion the polycondensation reaction will take place. Thus, the small droplets of the water-immiscible phase will be surrounded by the microcapsule wall formed by polycondensation of the isocyanate and the polyalcohol or polyamine as starting materials. Conversely, if the material to be encapsulated is hydrophilic, it will be included in the aqueous phase and the mixture of the two phases converted into a water-in-oil emulsion. The polycondensation reaction will then form microcapsule walls surrounding the droplets of water-miscible phase. Suitable emulsifiers are often utilized to aid in the preparation of, and to stabilise, the emulsion.

Suitable raw materials and processes for preparing microcapsules by polycondensation are described in U.S. Pat. No. 4,640,709 and the literature described therein. As is exemplified therein, and also in U.S. Pat. No. 6,133,197, polyurea and polyurethane microcapsules are often used for rugged applications, such as for encapsulation of agrochemicals e.g. herbicides and pesticides, where slow time-release is desired to set the agents free. For such applications the microcapsules also require a relatively high mechanical strength. For the polycondensation reaction a wide variety of suitable diisocyanate and symmetrical triisocyanate starting materials is disclosed in the prior art.

For the release of benefit agents intended for laundry, washing, cleaning, surface care and personal and skin care no polyurea or polyurethane microcapsules have thus far been applied. For such applications quicker and easier release and/or less mechanical strength are often desirable. Also it would be desirable to more precisely influence the capsule wall permeability and other capsule wall properties to achieve the desired release profile and consumer benefits

SUMMARY OF THE INVENTION

It has been found that polyurea or polyurethane microcapsules are very suitable for carrying various kinds of hydrophobic or hydrophilic benefit agents that are suitable for use in products intended for application to animate and inanimate surfaces.

In one embodiment of the invention a process is disclosed for the preparation of an encapsulated fragrance wherein the encapsulating wall material contains one or more an isocyanate, polyisocyanate, oligomer, or pre-polymer.

In another embodiment of the invention a process is disclosed for the preparation of an encapsulated fragrance wherein the encapsulating wall material may contain one or more difunctional isocyanate, or isocyanate oligmer, or pre-polymer, ymer, such as, polyisocyanate and a cross linker material such as polyamine and polyol.

In another embodiment of the invention a process is disclosed for the preparation of an encapsulated fragrance wherein encapsulated fragrance is cured at a temperature greater than about 55° C.

In another embodiment of the invention a process is disclosed for the preparation of an encapsulated fragrance wherein the cross linker material such as polyamine is added at 35° C.

In another embodiment of the invention a process is disclosed for the preparation of an encapsulated fragrance wherein the wall polymer level of the encapsulated fragrance wall is from about 5 to about 0.1% of the total capsules suspension, from about 2.5 to about 0.1% of the total capsules suspension, from about 2.0 to about 0.5% of the total capsules suspension, from about 1.5 to about 1% of the total capsules suspension In another embodiment of the invention a process is disclosed for the preparation of an encapsulated fragrance wherein the wall polymer level of the encapsulated fragrance wall is from about 15 to about 0.1% of the total capsules suspension, preferably from about 10% to about 1% most preferably from about 5 to about 2% of the total capsules suspension.

In another embodiment of the invention a process is disclosed for the preparation of an encapsulated fragrance wherein the amount of encapsulated fragrance oil is from about 80 to about 5% of the total capsules suspension, preferably from about 60% to about 10% most preferably from about 50 to about 20% of the total capsules suspension.

The present invention is well suited for use in rinse off products, which are products that are applied to a substrate and then removed in some manner. Especially preferred products that use the cationic coated polymer encapsulated fragrance or the present invention include, without limitation, hair and pet shampoos, hair conditioners, laundry detergents, fabric conditioners and the like. The fragrance capsules prepared from the present invention can also be used without additional coating. These and other embodiments of the present invention will become apparent upon referring to the following figure and description of the invention.

DETAILED DESCRIPTION OF THE INVENTION

For the purposes of this invention the isocyanate starting material is a polyisocyanate, which can be aromatic, aliphatic, linear, branched, or cyclic. As long as they are water insoluble, they can be used in the current invention. A preferred class is aromatic polyisocyanate that have the generic structure and its structural isomer;

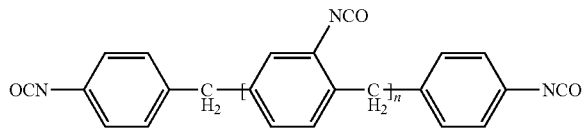

Where n can vary from zero to a desired number depending the type of polyamine or polyol used. For the purpose of this invention, the number, of n is limited to less than 6. The starting polyisocyanate may also be a mixture of polyisocyanates where the value of n can vary from 0 to 6. In the case where the starting polyisocyanate is a mixture of various polyisocyanate, the average value of n preferably falls in between 0.5 and 1.5

Example of polyisocyanate are Lupranate®M20 (BASF), where the average n is 0.7, PAPI 27 (Dow Chemical) where the where the average n is 0.7, Mondur MR (Bayer) where the average n is 0.8, Mondur MR Light (Bayer) where the average n is 0.8, and Mondur 489 (Bayer) where the average n is 1.0.

In general, the average MW of polyisocyanate in the formulation varies from 1000 to 250 and preferable from 500 to 275.

In general, the range of polyisocyanate concentration in the formulation varies from 10% to 0.1% and preferable from 5% to 0.25%

Examples of amines that can be used in the present inventions are diamines and polyamines. Water soluble diamine or amine salt or polyamines or polyamines salts are preferred as the amine is usually present in the aqueous phase. One class of such amine is of the type,

Where n is >=1, when n is 1, the amine is a diamine, ethylene diamine. When n=2, the amine is diamine propane and so on. For the purpose of this invention, the preferred n is 6, where the amine is a hexamethylene diamine.

Amines which have a functionality greater than 2, but less than 3 and which may provide a degree of cross linking in the shell wall are the polyalykylene polyamines of the type,

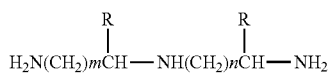

where R equals hydrogen or —CH$_3$, m is 1-5 and n is 1-5, e.g., diethylene triamine, triethylene tetraamine and the like.

Another class of polyamine that can be used in the invention is polyetheramines. They contain primary amino groups attached to the end of a polyether backbone. The polyether backbone is normally based on either propylene oxide (PO), ethylene oxide (EO), or mixed PO/EO. The either amine can be of monoamine, diamines, and triamine based on this core structure. An example is,

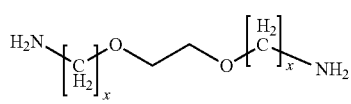

Examples are JEFFAMINE® EDR-148 (where x=2) JEFFAMINE® EDR-176 (where x=3) from the (Huntsman).

Another polyether amines include the JEFFAMINE® ED Series, JEFFAMINE® TRIAMINES. A wide range of polyetheramines may be selected by those skilled in the art.

In general, the range of diamine or polyamine concentration or the total amine concentration in the formulation varies from 5% to 0.1% and preferable from 2% to 0.25%

For the purpose of this invention, an emulsifier is a surface active agent that allows the emulsification of the oil phase into the aqueous phase. It can be incorporated either in the oil or aqueous phase depending on the HLB of the surfactant. The function of the dispersant is to function as a protective colloid to stabilize the formed emulsion or capsules dispersion. The emulsifier or dispersant can be used along and together in the invention as long as stable capsule formulation is obtained. Furthermore, nonionic and anionic surfactants and emulsifiers are preferred.

Examples of emulsifiers are alcohol ethoxylates, nonylphenol ethoxylates, salts of long chain alkylbenzene sulfonates, block copolymers of propylene oxide and ethylene oxide.

Especially preferred surfactants are Ethylan™ TD-60, Witconate 90 from Akzo Nobel, and Tergitol NP7, Tergitol XD, Tergitol NP40 and Tergitol 15-S-20 available from Union Carbide.

In general, the range of surfactant concentration in the formulation varies from 6% to 0.1% and preferable from 2% to 0.25%

A wide range of dispersant or protective colloid may be use in the formulation. Suitable material include one or more of salt of alkyl naphthalene sulfonate condensate, polyacrylates, methyl cellulose, carboxymethyl cellulose, polyvinyl alcohol, polyacrylamide, poly(methylvinyl ether/maleic anhydride), graft copolymers of polyvinyl alchol, and methylvinyl ether/maleic acid, (hydrolyzed methylvinyl ether/maleic anhydride), see U.S. Pat. No. 4,448,929. which is hereby incorporated by reference herein) and alkali metal or alkaline ether metal ligonosulfonates. Preferred dispersants is selected from sodium salt of alkyl naphthalene sulfonate condensate, polyvinyl alcohol, carboxymethyl cellulose. For fragrance applications, the lighter color polyvinyl alcohol, carboxymethyl cellulose is more preferred if satisfactory stability is obtainable.

In general, the range of dispersant concentration is the formulation varies from 5% to 0.1% and preferable from 2% to 0.25%

Microcapsules having a polyurethane or polyurea capsule wall are very suitable to carry a variety of benefit agents to be used in products for application to all kinds of surfaces. On the one hand surfaces may be inanimate, such as hard surfaces found in and around the house e.g. wooden, metal, ceramic, glass and paint surfaces, or soft surfaces such as clothing, carpets, curtains and other textiles. On the other hand, such surfaces may be animate surfaces, more particularly surfaces of a human or animal body i.e. human or animal skin and hair. For the purposes of this invention animate surfaces do not include plant surfaces.

The rinse-off products that are advantageously used with the polymer encapsulated fragrance of the present invention include laundry detergents, fabric softeners, bleaches, brighteners, personal care products such as shampoos, rinses, creams, body washes and the like. These may be liquids, solids, pastes, or gels, of any physical form. Also included in the use of the encapsulated fragrance are applications where a second active ingredient is included to provide additional benefits for an application. The additional beneficial ingredients include fabric softening ingredients, skin moisturizers, sunscreen, insect repellent and other ingredients as may be helpful in a given application. Also included are the beneficial agents alone, that is without the fragrance.

Products intended for application to a surface are generally intended for washing/cleaning or for caring/protecting or both. Examples are cleaning products for hard surfaces or textiles, caring/protection products like polishes and waxes for delicate surfaces such as wood, car paint and leather, laundry softening agents, antisoiling agents, water repelling agents, and the like. Examples of products intended for tho human skin are bath and shower products and shampoo for skin and hair cleansing, and all kinds of skin and hair care/protection products such as hair conditioners, hand and body lotions and creams, lip care products, deodorants and antiperspirants, make up products and the like.

It has been found that polyurethane or polyurea microcapsules are very suitable for carrying various kinds of hydrophobic or hydrophilic benefit agents that are suitable for use in products intended for application to animate and inanimate surfaces.

In one embodiment of the invention a process is disclosed for the preparation of an encapsulated fragrance wherein the encapsulating wall material contains one or more organic polyisocyanate.

In another embodiment of the invention a process is disclosed for the preparation of an encapsulated fragrance wherein the encapsulating wall material contains a polyisocyanate monomer and a crosslinker material such polyamine and polyol.

In another embodiment of the invention a process is disclosed for the preparation of an encapsulated fragrance wherein encapsulated fragrance is cured at a temperature greater than about 55° C.

In another embodiment of the invention a process is disclosed for the preparation of an encapsulated fragrance wherein the cross linker material such as polyamine is added at 35° C.

In another embodiment of the invention a process disclosed for the preparation of an encapsulated fragrance wherein the wall polymer level of the encapsulated fragrance wall is from about 5 to about 0.1% of the total capsules suspension, from about 2.5 to about 0.1% of the total capsules suspension, from about 2.0 to about 0.5% of the total capsules suspension, from about 1.5 to about 1% of the total capsules suspension.

In another embodiment of the invention a process is disclosed for the preparation of an encapsulated fragrance wherein the wall polymer level of the encapsulated fragrance wall is from about 15 to about 0.1% of the total capsules suspension, preferably from about 10% to about 1% most preferably from about 5 to about 2% of the total capsules suspension.

In another embodiment of the invention a process is disclosed for the preparation of an encapsulated fragrance wherein the polyisocyanate level of the encapsulated fragrance wall is from about 10 to about 0.1% of the total capsules suspension, preferably from about 7.5% to about 1% most preferably from about 3.5 to about 1.5% of the total capsules suspension.

In another embodiment of the invention a process is disclosed for the preparation of an encapsulated fragrance wherein the polyamine level of the encapsulated fragrance wall is from about 5 to about 0.1% of the total capsules suspension, preferably from about 3% to about 0.25% most preferably from about 2 to about 0.5% of the total capsules suspension.

In another embodiment of the invention a process is disclosed for the preparation of an encapsulated fragrance wherein the stiochiometry of the polyamine and polyisocyanate can be manipulated to give reduced amount polyisocyanate in the prepared capsule slurry. The stiochimetry of the polyamine to isocyanate will vary from 1 to 1, (one amine group per one isocyanate group), preferably from 2:1, (two amine groups per one isocyanate group) and most preferably from 4 to 1 two amine groups per one isocyanate group.

Specifically, by adding excess amount of polyamine can drive the polyurea formation toward more completion and less residual amount of polyisocyanate. The reaction stoichiometry requires one amine group per one isocyanate group. This is can be illustrated using Luprante® M20 and hexamethylenediamine (HMDA). The average MW of Luprante M20 is 360 and the isocyanate functionality is 2.7. In case of HMDA, the MW is 116.21 and the amine functionality is 2. Thus the stiochimetry of the system suggest that for each gram of HMDA, we need 2.23 g of Luprante. The amount of amine will be in excess if more than 1 g of HMDA is used per 2.23 g of Luprante M20. We have found that the amount of residual isocyanate can be significantly reduced by adding excess amount of amine reactant.

In another embodiment of the invention a process is disclosed for the preparation of an encapsulated fragrance wherein the amount of encapsulated fragrance oil is from about 80 to about 5% of the total capsules suspension, preferably from about 60% to about 10% most preferably from about 50 to about 20% of the total capsule suspension.

In another embodiment of the invention a process is disclosed for the preparation of an encapsulated fragrance wherein the wall polymer level of the encapsulated fragrance wall is from about 5 to about 0.1% of the total capsules suspension, from about 2.5 to about 0.1% of the total capsules suspension, from about 2.0 to about 0.5% of the total capsules suspension, from about 1.5 to about 1% of the total capsules suspension.

Cleaning and cleansing compositions will comprise one or more surfactants that may be chosen from anionic, cationic, nonionic, zwitterionic and amphoteric surfactants known in the art. For cleansing composition for skin or hair the surfactants must obviously meet the condition of being suitable for topical application.

The compositions according to the invention may optionally comprise a variety of components known in the art and adapted to their specific use. Thus, compositions intended for inanimate surfaces may comprise components such as builders, sequestrants, hydrotropes, organic solvents, pH regulation components such as organic or inorganic acids and/or bases, thickening agents, chlorine or peroxide bleaches, laundry softening agents, scouring agents, biocides, colouring agents, pearlescents, preservatives, perfumes. Compositions intended for application may contain a variety of vehicles suitable for topical application and a variety of benefit agents for skin or hair.

The microcapsules used in the compositions according to the invention are prepared using polycondensation processes known in the art for preparing polyurethane or polyurea microcapsules carried out in an oil-in-water or water-in-oil emulsion.

For the encapsulation process to take place the water-immiscible (organic) phase and the aqueous phase are converted into an emulsion using mixing equipment known in the art for such processes, particularly high shear mixing equipment. As is well known in the art, the mixing process determines the droplet size of the emulsion and thereby the microcapsule particle size. The mixing conditions are preferably chosen such that the average droplet size and therefore the median diameter (volumetric average particle size) of the microcapsules is between 0.1 and 500 µm, preferably at or below 300

μm, more preferably at or below 150 μm, most preferably at or below 50 μm. An emulsifier is usefully added to help in the formation of a suitable emulsion, particularly if a low droplet size (and thus microcapsule size) is desired. Optionally a dispersant may be added to further stabilize the emulsion and keep the microcapsules dispersed after their formation. Preferably, a dispersing agent is added which alio functions to obtaining the desired droplet size and, if desired, keep the microcapsules in suspension after their formation.

By choosing the relative amount of each of the phases, and a suitable emulsifier and/or dispersant as required, the emulsion can be either an oil-in-water or a water-in-oil emulsion, whereby the discontinuous phase will form the microcapsule content.

The reaction conditions required for the polycondensation reaction to take place efficiently are again well known in the art. Depending on the reagents, a reaction temperature between 20° and 90° C. is generally suitable, preferably between 50° and 85° C. The pH of the starting emulsion is preferably chosen between 4 and 10 and is largely determined the by the amount of amine used.

To optimize the performance of the capsules slurry, it is sometime desirable to explore experimental conditions under which the cross-link diamine or polyamine is added. We have surprisingly found that the performance of the capsules can be greatly improved when the diamine or polyamine is added at 35° C.

Often, it is necessary to cure the capsules slurry at evaluate temperature to drive a polymerization reaction to completion leading to lower free monomer concentration and maybe better performance. But one of the problems often encountered is the high viscosity of the capsule after the capsule is cured at higher temperature. We have surprisingly discover that by using a mixture of polyvinyl alcohol and anionic dispersant, Morwel D-425, that a free flowing slurry was obtained after the capsule was cured at 90° C.

Active Materials

The Clog P of many perfume ingredients has been reported, for example, the Ponoma92 database, available from Daylight Chemical Information Systems, Inc. (Daylight CIS) Irvine, Calif. The values are most conveniently calculated using Clog P program also available from Daylight CIS. The program also lists experimentally determined logP values when available from the Pomona database. The calculated logP (Clog P) is normally determined by the fragment approach on Hansch and Leo (A. Leo, in Comprehensive Medicinal Chemistry, Vol. 4, C. Hansch, P. G. Sammens, J. B. Taylor and C. A. Ransd™, Editiors, p. 295 Pergamon Press, 1990). This approach is based upon the chemical structure of the fragrance ingredient and takes into account the numbers and types of atoms, the atom connectivity and chemical bonding. The Clog P values which are most reliable and widely used estimates for this physiochemical property can be used instead of the experimental LogP values useful in the present invention. Further information regarding Clog P and logP values can be found in U.S. Pat. No. 5,500,138. It should be noted that the logP or Clog P normally referred to is the Octanol—Water partition coefficient. However, logP or Clog P values may also be defined for other Solvent—Water systems. These values are normally linearly related to the Octanol—Water logP or Clog P values. Thus, while the invention is described below in terms of the Octanol—Writer partition coefficient, it should be recognized that it may be described using any desired Solvent—Water partition coefficient using an appropriate transformation.

Fragrance materials with lower logP or Clog P, these terms will be used interchangeably from this point forward throughout the specification, normally exhibit higher aqueous solubility. Thus, when these materials are in the core of a capsule which is placed in an aqueous system, they will have a greater tendency to diffuse into the base if the shell wall is permeable to the fragrance materials. Without wishing to be bound by theory, it is believed that normally the mechanism of leaching from the capsule proceeds in three steps in an aqueous base. First, fragrance dissolves into the water that hydrates the shell Second, the dissolved fragrance diffuses through the shell wall into the bulk water phase. Third, the fragrance in the water phase is absorbed by the hydrophobic portions of the surfactant dispersed in the base, thus allowing leaching to continue. A similar process occurs in situations where the aqueous base does not contain a surfactant but rather a flavor absorbing lipid phase. The flavor absorbing lipid phases are found in a wide variety of food products such as mayonnaise, dressings, soups, baked goods, batters and the like. Lipids that could absorb flavors include but are not limited to soybean oil, corn oil, cottonseed oil, sunflower oil, lard, tallow and the like.

This situation may be improved by one embodiment of the present invention which involves the use of a vast preponderance of high Clog P fragrance materials. In this embodiment of the invention greater than about 60 weight percent of the fragrance materials have a Clog P of greater than 3.3. In another highly preferred embodiment of the invention more than 80 weight percent of the fragrances have a Clog P value of greater than about 4.0. In the most preferred embodiment of the invention more than 90% of the fragrances have a Clog P value of greater than about 4.5. Use of fragrance materials as described previously reduces the diffusion of fragrance through the capsule wall and into the base under specific time, temperature, and concentration conditions.

It should be noted that while Clog P and aqueous solubility are roughly correlated, there are materials with similar Clog P yet very different aqueous solubility. Clog P is the traditionally used measure of hydrophilicity in perfumery, and forms the basis for describing the invention. However, the invention may be further refined by the embodiment that greater than 60 weight percent of the fragrance materials have a Clog P of greater than 3.3 and a water solubility of less than 350 ppm. In another highly preferred embodiment of the invention more than 80 weight percent of the fragrances have a Clog P of greater than 4.0 and a water solubility of less than 100 ppm. In the most preferred embodiment of the invention more than 90% of the fragrances have a Clog P value of greater than about 4.5 and a water solubility of less than 20 ppm. In any case, selection of materials having lower water solubility is preferred.

The following fragrance ingredients provided in Table I are among those suitable for inclusion within the capsule of the present invention:

TABLE 1

| PERFUME INGREDIENTS | CLOG P |
|---|---|
| Allyl cyclohexane propionate | 3.935 |
| Ambrettolide | 6.261 |
| Amyl benzoate | 3.417 |
| Amyl cinnamate | 3.771 |
| Amyl cinnamic aldehyde | 4.324 |
| Amyl cinnamic aldehyde dimethyl acetal | 4.033 |
| Iso-amyl salicylate | 4.601 |
| Aurantiol (Trade name for Hydroxycitronellal-methylanthranilate) | 4.216 |
| Benzyl salicylate | 4.383 |
| para-tert-Butyl cyclohexyl acetate | 4.019 |

TABLE 1-continued

| PERFUME INGREDIENTS | CLOG P |
|---|---|
| Iso butyl quinoline | 4.193 |
| beta-Caryophyllene | 6.333 |
| Cadinene | 7.346 |
| Cedrol | 4.530 |
| Cedryl acetate | 5.436 |
| Cedryl formate | 5.070 |
| Cinnamyl cinnamate | 5.480 |
| Cyclohexyl salicylate | 5.265 |
| Cyclamen aldehyde | 3.680 |
| Diphenyl methane | 4.059 |
| Diphenyl oxide | 4.240 |
| Dodecalactone | 4.359 |
| Iso E Super (Trade name for 1-(1,2,3,4,5,6,7,8-Octahydro-2,3,8,8-tetramethyl-2-naphthalenyl)-ethanone) | 3.455 |
| Ethylene brassylate | 4.554 |
| Ethyl undecylenate | 4.888 |
| Exaltolide (Trade name for 15-Hydroxyentadecanloic acid, lactone) | 5.346 |
| Galaxolide (Trade name for 1,3,4,6,7,8-Hexahydro-4,6,6,7,8,8-hexamethylcyclopenta-gamma-2-benzopyran) | 5.482 |
| Geranyl anthranilate | 4.216 |
| Geranyl phenyl acetate | 5.233 |
| Hexadecanolide | 6.805 |
| Hexenyl salicylate | 4.716 |
| Hexyl cinnamic aldehyde | 5.473 |
| Hexyl salicylate | 5.260 |
| Alpha-Irone | 3.820 |
| Lilial (Trade name for para-tertiary-Butyl-alpha-methyl hydrocinnamic aldehyde) | 3.858 |
| Linalyl benzoate | 5.233 |
| Methyl dihydrojasmone | 4.843 |
| Gamma-n-Methyl ionone | 4.309 |
| Musk indanone | 5.458 |
| Musk tibetine | 3.831 |
| Oxahexadecanolide-10 | 4.336 |
| Oxahexadecanolide-11 | 4.336 |
| Patchouli alcohol | 4.530 |
| Phantolide (Trade name for 5-Acetyl-1,1,2,3,3,6-hexamethyl indan) | 5.977 |
| Phenyl ethyl benzoate | 4.058 |
| Phenylethylphenylacetate | 3.767 |
| Phenyl heptanol | 3.478 |
| Alpha- Santalol | 3.800 |
| Thibetolide (Trade name for 15-Hydroxypentadecanoic acid, lactone) | 6.246 |
| Delta-Undecalactone | 3.830 |
| Gamma-Undecalactone | 4.140 |
| Vetiveryl acetate | 4.882 |
| Ylangene | 6.268 |

The higher Clog P materials are preferred, meaning that those materials with a Clog P value of 4.5 are preferred over those fragrance materials with a Clog P of 4; and those materials are preferred over the fragrance materials with a Clog P of 3.3.

The fragrance formulation of the present invention should have at least about 60 weight percent of materials with Clog P greater than 3.3, preferably greater than about 80 and more preferably greater than about 90 weight percent of materials with Clog P greater than 4.5.

Those with skill in the art appreciate that fragrance formulations are frequently complex mixtures of many fragrance ingredients. A perfumer commonly has several thousand fragrance chemicals to work from. Those with skill in the art appreciate that the present invention may contain a single ingredient, but it is much more likely that the present invention will comprise at least eight or more fragrance chemicals, more likely to contain twelve or more and often twenty or more fragrance chemicals. The present invention also contemplates the use of complex fragrance formulations containing fifty or more fragrance chemicals, seventy five or more or even a hundred or more fragrance chemicals in a fragrance formulation.

Preferred fragrance materials will have both high Clog P and high vapor pressure. Among those having these properties include: para cymene, caphene, mandarinal firm, Vivaldie™, terpinene, Verdox™, fenchyl acetate, cyclohcxyl isovalerate, manzanate, myrcene, herbavert, isobutyl isobutyrate, tetrahydrocitral, ocimene and caryophyllene.

As described herein, the present invention is well suited for use in a variety of well-known consumer products such as laundry detergent and fabric softeners, liquid dish detergents, tumble dryer sheets, oral care products, personal care products, foodstuffs, beverages, automatic dish detergents, toothpastes, mouthwashs, as well as hair shampoos and conditioners. These products employ surfactant and emulsifying systems that aro well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,40,499, 5,288,417, and 4,767,547, 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,706,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,613,523, 5,275,755, 5,085,857, 4,673,568, 4,387,090 and 4,705,681. Toothpastes and other oral care products that can employ the present invention include those described in U.S. Pat. Nos. 6,361,761, 6,616,915, 6,696,044, 6,193,956, 6,132,702, 6,004,538, 5,939,080, 5,885,554, 6,149,894, 5,505,933, 5,503,823, 5,472,685, 5,300,283 and 6,770,264.

In addition to the fragrance materials that are to be encapsulated in the present invention, the present invention also contemplates the incorporation of solvent materials. The solvent materials are hydrophobic materials that are miscible in the fragrance materials used in the present invention. Suitable solvents are those having reasonable affinity for the fragrance chemicals and a Clog P greater than 3.3, preferably greater than 6 and most preferably greater that 10. Suitable materials include, but are not limited to triglyceride oil, mono and diglycerides, mineral oil, silicone oil, diethyl phthalate, polyalpa olefins, castor oil and isopropyl myristate. In a highly preferred embodiment the solvent materials are combined with fragrance materials that have high Clog P values as set forth above. It should De noted that selecting a solvent and fragrance with high affinity for each other will result in the most pronounced improvement in stability. This specific affinity may be measured by determining the Solvent—Water partition coefficient for the fragrance material. Appropriate solvents may be selected from the following non-limiting list:

Mono-, di- and tri-esters, and mixtures thereof, of fatty acids and glycerine. The fatty acid chain can range from C4-C26. Also, the fatty acid chain can have any level of unsaturation. For instance capric/caprylic triglyceride known as Neobee M5 (Stepan Corporation). Other suitable examples are the Capmul series by Abitec Corporation. For instance, Capmul MCM.

Isopropyl myristate

Fatty acid esters of polyglycerol oligomers: R2CO—[OCH2—CH(OCOR1)—CH2O-]n, where R1 and R2 can be H or C4-26 aliphatic chains, or mixtures thereof, and n ranges between 2-50, preferably 2-30.

Nonionic fatty alcohol alkoxylates like the Neodol surfactants by BASF, the Dobanol surfactants by Shell Corporation or the BioSoft surfactants by Stepan. The alkoxy group being ethoxy, propoxy, butoxy, or mixtures thereof. In addition, these surfactants can be end-capped with methyl groups in order to increase their hydrophobicity.

Di- and tri-fatty acid chain containing nonionic, anionic and cationic surfactants, and mixtures thereof.

Fatty acid esters of polyethylene glycol, polypropylene glycol, and polybutylene glycol, or mixtures thereof.

Polyalphaolefins such as the ExxonMobil PureSym™ PAO line

Esters such as the ExxonMobil PureSyn™ Esters

Mineral oil

Silicone oils such polydimethyl siloxane and polydimethylcyclosiloxane

Diethyl phthalate

Di-isodecyl adipate

The level of solvent in the core of the encapsulated fragrance material should be greater than about 10 weight percent, preferably greater than about 30 weight percent and most preferably greater than about 70 weight percent. In addition to the solvent it is preferred that higher Clog P fragrance materials are employed. It is preferred that greater than about 60 weight percent, preferably greater than 80 and more preferably greater than about 90 weight percent of the fragrance chemicals have Clog P values of greater than about 3.3, preferably greater than about 4 and most preferably greater than about 4.5. Those with skill in the art will appreciate that many formulations can be created employing various solvents and fragrance chemicals. The use of a high level of high Clog P fragrance chemicals will likely require a lower level of hydrophobic solvent than fragrance chemicals with lower Clog P to achieve similar performance stability. As those with skill in the art will appreciate, in a highly preferred embodiment high Clog P fragrance chemicals and hydrophobic solvents comprise greater than about 80, preferably more than about 90 and most preferably greater than about 95 weight percent of the fragrance composition. As discussed above, specific Clog P values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

It has also been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymers may be selected from the non-limiting group below:

Copolymers of ethylene. Copolymers of ethylene and vinyl acetate (Elvax polymers by DOW Corporation). Copolymers of ethylene and vinyl alcohol (EVAL polymers by Kuraray). Ethylene/Acrylic elastomers such as Valnac polymers by Dupont).

Poly vinyl polymers, such as poly vinyl acetate.

Alkyl-substituted cellulose, such as ethyl cellulose (Ethocel made by DOW Corporation), hydroxypropyl celluloses (Klucel polymers by Hercules); cellulose acetate butyrate available from Eastman Chemical.

Polyacrylates. Examples being (i) Amphomer, Demacryl LT and Dermacryl 79, made by National Starch and Chemical Company, (ii) the Amerhold polymers by Amerchol Corporation, and (iii) Acudyne 258 by ISP Corporation.

Copolymers of acrylic or methacrylic acid and fatty esters of acrylic or methacrylic acid. These are side-chain crystallizing. Typical polymers of this type are those listed in U.S. Pat. Nos. 4,830,855, 5,665,822, 5,783,302, 6,255,367 and 6,492,462. Examples of such polymers are the Intelimer Polymers, made by Landec Corporation.

Polypropylene oxide.

Polybutylene oxide of poly(tetrahydrofuran).

Polyethylene terephthalate.

Polyurethanes (Dynam X by National Starch)

Alkyl esters of poly(methyl vinyl ether)—maleic anhydride copolymers, such as the Gantrez copolymers and Omnirez 2000 by ISP Corporation.

Carboxylic acid esters of polyamines. Examples of this are ester-terminated polyamide (ETPA) made by Arizona Chemical Company.

Poly vinyl pyrrolidone (Luviskol series of BASF).

Block copolymers of ethylene oxide, propylene oxide and/or butylenes oxide. These are known as the Pluronic and Synperonic polymers/dispersants by BASF.

Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

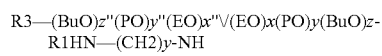

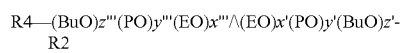

where R1, R2, R3, R4 is H or any alkyl of fatty alkyl chain group. Examples of such polymers are the commercially known as Tetronics by BASF Corporation.

We have also discovered that when capsules having cores containing a very large proportion of solvents with the appropriate Clog P values; and/or with the high Clog P fragrance chemicals described above the encapsulated materials are actually capable of absorbing fragrance chemicals from surfactant-containing product bases. As is well appreciated by those with skill in the art, products such as, but not limited to fabric softeners, laundry detergents, toothpastes, bleaching products, shampoos and hair conditioners contain in their base formulas functional materials such as surfactants, emulsifying agents, detergent builders, whiteners, and the like along with fragrance chemicals. These products often aggressively absorb fragrance ingredients, most often due to the partially hydrophobic surfactant. Likewise, many food products contain high levels of fats and other lipids which also absorb flavors.

Most consumer products are made using an aqueous base containing a surfactant, although some products use glycols, polyhydric alcohols, alcohols, or silicone oils as the dominant solvent or carrier. Absorption from these bases in also possible if the core is properly designed and used at the appropriate level in the base. Examples of these products include many deodorants and anti-perspirants.

In the product base the fragrance is used to provide the consumer with a pleasurable fragrance during and after using the product or to mask unpleasant odors from some of the functional ingredients used in the product. As stated above, one long standing problem with the use of fragrance in product bases is the loss of the fragrance before the optimal time for fragrance delivery. We have discovered that with the proper selection of solvent and/or fragrance chemicals in the capsule core, and the proper level of core usage, the capsule will successfully compete for the fragrance chemicals present in the aqueous product base during storage. Eventually the core absorbs a significant quantity of fragrance, and finally an equilibrium level of fragrance is established in the core which is specific to the starting core composition and concentration in the base, type and concentration of the fragrance materials in the base, base composition (especially surfactant type and concentration), and conditions of storage. This ability to load the capsule core with fragrance material from the product base, particularly those product bases that contain a high concentration of surfactant clearly indicates that with judicious selection of core composition good fragrance stability within the core can be achieved.

Therefore, in another embodiment of the present invention is a method for providing encapsulated fragrance products through the re-equilibration of the fragrance materials from the product base into the capsules. The process includes providing a product base containing fragrance materials and capsules with a permeable shell, the capsules containing a solvent as defined above or with high Clog P fragrance materials. The solvents and high Clog P fragrance materials have an affinity for the fragrance material. In order to absorb fragrance materials that previously are not present in the core of the capsules, to re-equilibrate into the capsule core it is preferred that the capsules contain some void space or contain some lower Clog P materials that can partition out of the capsule into product base. Capsule shells with the appropriate degree of permeability are described in the application.

As described above capsules loaded with solvent and or high Clog P fragrance materials will absorb other fragrance materials from the product. In this embodiment of the invention, the capsule cores compete with the surfactant and primarily aqueous media of the products for fragrance materials placed in the product bases during storage. Eventually the cores absorb a significant quantity of fragrance, and finally an equilibrium level of fragrance is established in the core which is specific to a given starting core composition and concentration in the base, type and concentration of fragrance materials in the base, base composition and conditions of storage. The self-loading of the cores in bases that have high concentrations of surfactants also indicates that by judicious core selection fragrance stability within the core can be achieved.

As used herein stability of the products is measured at room temperature or above over a period of at least a week. More preferably the capsules of the present invention are allowed to be stored at room temperature for more than about two weeks and preferably more than about a month.

More specifically, the present invention provides a method of encapsulating a fragrance material comprising:

providing a product base containing non-encapsulated fragrance material and surfactant material;

providing a permeable capsule wherein the permeable capsule contains greater than about 70 weight percent fragrance material having a Clog P value of greater than about 3.3 and/or suitable hydrophobic solvent; and allowing the non-encapsulated fragrance material and the permeable capsule material containing the fragrance material to come to equilibrium thereby transporting the non-encapsulated fragrance through the permeable shell wall into the interior of the capsule and retaining the fragrance contents of the permeable capsule.

In this embodiment of the invention a method for increasing the amount of a fragrance within a capsule comprising an aqueous base product that contains surfactant and fragrance, providing a capsule permeable to the fragrance when stored in the base, contained within said capsule greater than about 60 weight percent components selected from the group consisting of hydrophobic solvent and fragrance chemicals having a Clog P value of greater than about 3.3; storing the aqueous product base and the porous capsule for at least about a week, thereby allowing the fragrance chemicals provided in the aqueous base to be transported through the capsule wall. As further described, the selection of solvents and fragrance chemicals with correct Clog P values results in capsules with higher fragrance loading. The higher fragrance loading results in higher fragrance delivery than what was previously possible with fragrance provided in the aqueous base or provided in an oil included in the base. For example, when the capsules are employed in a fabric conditioner product it was discovered that the capsules of the present invention deposited fragrance as measured by the breaking of the capsules and the measurement of fragrance in the headspace to be more than 100% greater than fragrance alone or fragrance and solvent combinations deposited on the same cloth. In some instances the headspace measurement indicated an increase of more than 200 and even greater than about 300 percent when measuring fragrance in the headspace when employing the capsules with high Clog P materials and/or suitable solvents when compared to fragrance or fragrance solvent combinations.

In another embodiment of the present invention a sacrificial solvent is initially placed within the capsule. A sacrificial solvent is a solvent having t low Clog P value of less than about 3; generally from about 1 to about 2.75, preferably from about 1.25 to about 2.5, and most preferably from about 1.5 to about 2. If the Clog P of the sacrificial solvent is too low, the sacrificial solvents will be lost in the manufacture of the capsule materials. Suitable sacrificial solvents include benzyl acetate, and octanol. The level of sacrificial solvent used in the core should be greater than 10%, preferably greater than 20%, and most preferably greater than 30%. The remainder of the core is preferably composed of materials having a Clog P greater than 3.3, and more preferably greater than 4.0, and most preferably greater than 6.0.

The present invention provides a method of making capsules fragrance materials within the capsule comprising the steps of:

providing a sacrificial solvent having a Clog P value of from about 1 to about 3 in the capsule core at a level of at least 10%;

encapsulating the sacrificial solvent containing core with a permeable encapsulate material;

providing the encapsulated sacrificial solvent combining core in a liquid environment containing fragrance materials;

allowing the capsules containing the sacrificial sol vent to come to equilibrium with the environment containing the high Clog P fragrance material's;

whereby at least 20 weight percent of the sacrificial solvent migrates from the capsule into the environment.

Preferably more than 30 and more than 40 weight percent of the sacrificial solvent will migrate from the capsules to the environment, thereby allowing the capsules to increase the level of fragrance material inside the capsule by more than 10 weight percent, preferably more than 20 and most preferably more than 30 weight percent over the original weight of fragrance materials originally found inside the capsule.

The time for this migration of the sacrificial solvent from the interior of the permeable capsule to the environment, thereby creating space within the capsule for the high Clog P materials to migrate into the capsule is as short as seven to ten days. This means that under normal product manufacture, shipping and distribution, the sacrificial solvent will have sufficient time to migrate from the capsule interior, thereby creating free volume and allowing the preferred fragrance materials to migrate into the interior. Of course, longer periods of time will allow greater amounts of the sacrificial solvent to exit through the capsule wall and create more free volume and eventually a true equilibrium will occur where at a given temperature, the migration of sacrificial solvent out of the capsule and migration of fragrance material into the capsule will eventually end.

An important advantage of the migration technology is that capsules containing sacrificial solvent can be prepared in large quantities, and placed in various fragrance environments. This means that through the proper selection of fragrance materials, capsules and sacrificial solvent, encapsulated fragrance materials can be prepared without having to encapsulate each specific custom fragrance.

These and additional modifications and improvements of the present invention may also be apparent to those with ordinary skill in the art. The particular combinations of elements described and illustrated herein are intended only to represent only a certain embodiment of the present invention and are not intended to serve as limitations of alternative articles within the spirit and scope of the invention. As used herein all percentages are weight percent unless otherwise noted, ppm is understood to stand for parts per million, mL is understood to be milliliter, g is understood to be gram, and mol is understood to be mole. All materials are reported in weight percent unless noted otherwise. As used herein all percentages are understood to be weight percent.

Example 1

Preparation of Polyurea Capsule with Benzyl Acetate

Step 1. Preparation of the fragrance emulsion. One hundred twenty grams of benzyl acetate (BA, ClogP of 1.79) was weighed out and combined with 9.6 g of isocyanate monomer, Lupranate®M20 (BASF corporation, Wyandotte, Mich., USA) to form the oil phase. In a separate beaker, a 3% surfactant solution (160 g) was prepared by dissolving sufficient amount of Mowet D-425 (Akzo Nobel, Fort Worth, Tex., USA) in DI water. The oil phase was then emulsified into the aqueous phase to form the fragrance emulsion under shearing (Ultra Turrax®, T25 Basic, IKA® WERKE) at 6500 rpm for two minutes.

Step 2. Formation of fragrance capsules. The BA emulsion prepared in step 1 was placed in a round bottom vessel and to which 10.8 g of 40% hexamethylene diamine (HMDA) (INVISTA, Wichita, Kans., USA) was added under constant mixing with an overhead mixer. Formation of capsule was immediately visible by optical microscopy. The mixer speed was reduced after the addition of HMDA was complete. The capsule slurry was cured at room temperature for three hours.

The capsule can range from submicron to hundreds of microns depending on the emulsifier and shear rates used.

Other isocyanate monomers such as that PAPI* 27 (Dow Chemical, Midland, Mich.), Mondur MR (Bayer), Mondur MR Light (Bayer) and poly[(phenylisocyanate)-co-formaldehyde] (Aldrich Chemical, Milwaukee, Wis.) may be used in place of Lupranate M20. These polyisocyanates can be used interchangeably.

The amount of Morwet D-425 can also be varied from 0.5 to 4% depending on formulation need.

Example 2

Preparation of Polyurea Capsule with a Full Fragrance

Step 1. Preparation of fragrance emulsion. One hundred twenty grams of fragrance mixture containing a commercial fragrance Fresh Zion (International Flavors & Fragrances, Union Beach, N.J.) and Neobee (50/50) was weighed out and combined with 9.8 g of Lupranate®M20 and 1.6 g of Witconol TD-60 to form the oil phase. A 3% surfactant (D-425) solution (160 g) was prepared according to Example 1. The oil phase was emulsified into the aqueous phase to form the fragrance emulsion under shearing at 6500 rpm for two minutes.

Step 2. Formation of fragrance capsules. Fragrance capsule was formed immediately after the addition of HMDA as in Example 1 and was evident from microscopic observation. The capsule slurry was cured at room temperature.

Example 3

Preparation of Polyurea Capsule with a Full Fragrance with the Addition of HMDA at Elevated Temperature Step 1. Preparation of fragrance emulsion. One hundred twenty grams of fragrance mixture containing a commercial fragrance, Blue Touch Tom, (International Flavors & Fragrances, Union Beach, N.J.) and Neobee (80/20) was weighed out and combined with 9.8 g of Lupranate®M20 to form the oil phase. A 3% surfactant solution (160 g) was prepared according to example 1. The oil phase was emulsified into the aqueous phase to form the fragrance emulsion under shearing at 6500 rpm for two minutes.

Step 2. Formation and curing of capsules of fragrance capsules. The fragrance emulsion was heated to 35° C. before HMDA (10.8 g, 40%) was added drop wise. Fragrance capsule was immediately after the addition of HMDA. The capsule slurry was transferred into a round bottom vessel and the temperature was raised 55° C. and kept at 55° C. for 2 hours.

Example 4

Preparation of Cured Polyurea Capsule with a Full Fragrance and Adding HMDA at Elevated Temperature and Cured at Elevated Temperature Step 1. Preparation of fragrance emulsion. One hundred twenty grams of fragrance mixture containing Blue Touch Tom fragrance (International Flavors & Fragrances, Union Beach, N.J.) and Neobee (80/20) was weighed cut and combined with 9.8 g of Lupranate M20 to form the oil phase. A 3% surfactant solution (160 g) was prepared according to Example 1. The oil phase was emulsified into the aqueous phase to form the fragrance emulsion under shearing at 6500 rpm for two minutes.

Step 2. Formation and curing of capsules of fragrance capsules. The fragrance emulsion was heated to 35° C. before HMDA (10.8 g, 40%) was added drop wise. Fragrance capsule was immediately after the addition of HMDA. The capsule slurry was transferred into a round bottom vessel and the temperature was raised 55° C. and kept at 55° C. for 2 hours and then at 90° C. for 2 hours.

Example 5

Preparation of Cured Polyurea Capsule with Adjunct Cross-Linkers

Step 1. Preparation of fragrance emulsion. One hundred twenty grams of fragrance mixture containing Blue Touch Tom fragrance (International Flavors & Fragrances Inc. Union Beach, N.J.) and Neobee (80/20) was weighed out and combined with 9.8 g of Lupranate®M20 to form the oil phase. A 3% surfactant solution (160 g) was prepared according to Example 1. The oil phase was emulsified into the aqueous phase to form the fragrance emulsion under shearing at 6500 rpm for two minutes.

Step 2. Formation and curing of capsules of fragrance capsules. A mixture of HMDA (8.8 g, 40%) and polyetheramine, JEFFAMINE EDR-176 (0.88 g) (Huntsman, The Woodlands, Tex.) was used as the cross-linking reagent. The ratio of HMDA to ERT-176 was 80:20. The amine was added after the fragrance was heated to 35° C. Excellent capsules formed were evident from microscopic observation. The capsule slurry was transferred into a round bottom vessel and the temperature was raised 55° C. and it was kept at 55° C. for 2 hours.

Example 6

Preparation of Cured Polyurea Capsule with Reduced Polymer Wall Materials

Step 1. Preparation of fragrance emulsion. One hundred twenty grams of fragrance mixture containing Blue Touch Tom fragrance (International Flavors & Fragrances Inc. Union Beach, N.J.) and Neobee (80/20) was weighed out and combined with 4.8 g of Lupranate®M20 to form the oil phase. A 2% surfactant solution (160 g) was prepared according to Example 1. The oil phase was emulsified into the aqueous phase to form the fragrance emulsion under shearing at 6500 rpm for two minutes.

Step 2. Formation and curing of capsules of fragrance capsules. The fragrance emulsion was heated to 35° C. before HMDA (5.4 g, 40%) was added drop wise. Capsules were formed immediately. The slurry was transferred into a round bottom vessel and the temperature was raised 55° C. and it was kept at 55° C. and then at 90° C. for 2 hours.

Example 7

Preparation of Cured Polyurea Capsule with Lesser Polymer Wall Materials

The processes in Example 6 were repeated 3.24 g (40%) of Lupranate®M20 and 1.5 g of 40% HMDA.

Example 8

Stability Evaluation of Polyurea Capsules

The prepared polyurea capsules in example 1 and 2 were incorporated into a 9% cationic surfactant solution and the leaching of ingredient was monitored as a function of time at elevated temperature. The results are given in the figure below figure. It can be seen that over 75% of ingredient was still retained after 4 wks at 37° C. This demonstrates the polyurea capsules are quite effective in retaining both lower ClogP single ingredient and full fragrance materials.

Example 9

Encapsulation Performance of Polyurea Capsules

Capsule slurry of a commercial available fragrance, Blue Touch Tom, IFF, was prepared using the procedures described in example 3. The fragrance capsule slurry was further diluted with distilled water to yield a mixture containing 0.2% capsule slurry. One gram each of the diluted capsule slurry was directly applied to each side of a 4×6 fabric swatch. Two samples were prepared. The swatches were air-dried over night and the headspace of the fabrics was analyzed before and after stirring with stainless steel ball bearings to rupture intact capsules. The results are given in Table 1.

TABLE 1

Performance test results of polyurea capsules

| | SAMPLE 1 | | SAMPLE 2 | |
|---|---|---|---|---|
| | Unstirred | Stirred | Unstirred | Stirred |
| Headspace | 9695 | 35518 | 8300 | 40852 |
| Ratio Stirred/Unstirred | — | 2.7 | — | 3.9 |

It can be clearly seen that there is a dramatic increase in headspace after the capsules were disrupted by milling. This demonstrated that increased perfumery perception can be achieved once the capsules are deposited on fabric and ruptured by physical forces.

Example 10

Demonstration of the Perfumery Performance of Polyurea Capsules

To establish the performance of the polyurea capsules, the capsule slurry prepared in Example 3 was blended into a model rinse conditioner solution that contains 12% cationic surfactant. The fragrance load was 1% mat equivalent. For comparison, a similar solution was prepared using neat fragrance at 1%. The perfumery benefit of the capsules was evaluated by conducting a laundry experiment using accepted experimental protocols using European wash machine. Terry towels were used for the washing experiments and were air-dried overnight before being evaluated by panel of 12 judges. The fragrance intensity is rated from a LMS scale ranging from 0 to 30. A numerical value of 5 would suggest the fabric only produce very week intensity while a value of 30 indicates the subject generate a strong smell. The results are in Table 2.

TABLE 2

Contrasting the Sensory performance of capsules with that of neat fragrance

| Samples | Pre-rubbing intensity | Post-rubbing intensity | $I_{pre, capsule}/I_{pre, neat}$ | $I_{post, capsule}/I_{post, neat}$ |
|---|---|---|---|---|
| Neat | 3.3 | 3.9 | | |
| Polyurea capsule | 10.2 | 14.0 | 3.10 | 3.58 |

It is quite apparent the polyurea fragrance capsules produced much greater fragrance intensity at the pre-rubbing and post-rubbing stages stage. The increase in fragrance intensity is much more pronounced in the post rubbing stage. This demonstrates that the polyurea fragrance capsules prepared with the current invention are able to retain the fragrance effectively and are capable of delivering the full consumer benefits of the fragrance products.

Example 11

Demonstration of the Robust Storage Stability and Favorable Fragrance Release Profile the Polyurea Capsules This example will demonstrate the superior performance of the polyurea capsule over extended storage.

To conduct the study, two capsule slurries were prepared using the process described in example 3, but using a commercial fragrance, California, (International Flavors & Fragrances, Union Beach, N.J.). The capsule was blended into a model rinse conditioner solution that contains 12% cationic surfactant. The fragrance loading was at 1% neat equivalent in all cases. The samples were aged at 37° C. for up to 9 weeks in a temperature controlled oven. Laundry and sensor/experiments were conducted as protocols in Example 10 and the results are given in Table 3.

TABLE 3

Contrasting the Sensory performance of capsules with that of neat fragrance after extend storage

| Samples | Pre-rubbing intensity | Post-rubbing intensity | $I_{pre, capsule}/I_{pre, neat}$ | $I_{post, capsule}/I_{post, neat}$ |
|---|---|---|---|---|
| Neat | 3.2 | 3.3 | | |
| Polyurea capsule 1 | 7.0 | 15.7 | 2.18 | 4.75 |
| Polyurea capsule 2 | 12.0 | 15.8 | 3.75 | 4.78 |

It is quite clear that the polyurea fragrance capsules produced much greater fragrance intensity at the pre-rubbing and post-rubbing stages stage even after the samples are aged at 37° C. oven for 9 weeks. The increase in fragrance intensity is much more pronounced in the post rubbing stage. This demonstrates that the polyurea fragrance capsules prepared with the current invention are able to retain the fragrance effectively and are capable of delivering the full consumer benefits of the fragrance products.

Example 12

Demonstration of the Favorable Fragrance Release Profile in Polyurea Capsules This example will demonstrate the superior performance of the polyurea capsule over a melamine formaldehyde capsules commercially available from IFF.

To conduct the study, capsule slurry was prepared using the process described in Example 3 using a commercial fragrance, Blue Touch Tom, (IFF, Union Beach N.J.). Capsule slurry was prepared using the same fragrance using a patented and widely used aminoplast capsules. To conduct the comparative study, the capsule was blended into a model rinse conditioner solution that contains 12% cationic surfactant. The fragrance loading was at 1% neat equivalent in both cases. A control sample was made using neat fragrance at the same loading. Laundry and sensory experiments were conducted as protocols in example 10 and the results are given in Table 4.

TABLE 4

Contrasting the Sensory performance of polyurea capsule with that of aminoplast capsule

| Samples | Pre-rubbing intensity | Post-rubbing intensity | $I_{pre, capsule}/I_{pre, neat}$ | $I_{post, capsule}/I_{post, neat}$ |
|---|---|---|---|---|
| Neat | 3.3 | 3.9 | | |
| Aminoplast capsule | 5.4 | 14.7 | 1.64 | 3.77 |
| Polyurea capsule | 10.2 | 14.0 | 3.09 | 3.59 |

It is quite clear that the polyurea fragrance capsules produced fragrance intensity that is three times of the neat and nearly twice that of the aminoplast capsule at the pre-rubbing stage. At the post-rubbing stage, it also produced three time intensity of that and comparable intensity to that of the aminoplast capsule. This demonstrates that the polyurea fragrance capsules prepared with the current invention are able to retain the fragrance effectively and has a much favorable release profile as it can delivery the fragrance benefit without mechanical perturbation.

Example 13

Demonstration of the Effect of Curing Temperature on Capsule Performance

This example will demonstrate the efforts of curing temperature on the performance of polyurea capsule over extended storages.

Since fragrance molecules are highly volatile, it is preferable that an encapsulation process can be developed that can be practice at lower temperature while maintaining good performance. In all the published literature the capsules that performed well were cured at elevated temperature as higher temperature will force a chemical reaction toward more completion leading to better stability. We however, surprisingly discovered that the polyurea capsules can performance very well under lower curing temperatures.

To conduct the study, four capsule slurries were prepared using the process described in example 3 using a commercial fragrance, Blue Touch Tom, (International Flavors & Fragrances, Union Beach, N.J.). The capsules were first cured at 55° C. and then cured and 55, 65, 75 and 80° C. respectively for 2 more hours. Four samples were then prepared by blending the capsules into model rinse conditioner solution that contains 24% cationic surfactant. The fragrance loading was at 1% neat equivalent in all cases. The samples were aged at 37° C. for 8 weeks in a temperature controlled oven. Laundry and sensory experiments were conducted as protocols in example 10 using US wash machines and the results are given in Table 5.

TABLE 5

Comparing the sensory performance of polyurea capsule prepared at different curing temperatures

| Samples | Pre-rubbing intensity | Post-rubbing intensity | $I_{pre, capsule}/I_{pre, neat}$ | $I_{post, capsule}/I_{post, neat}$ |
|---|---|---|---|---|
| Neat | 2.5 | 2.6 | | |
| capsule cured at 55° C. | 4.4 | 13.8 | 1.76 | 5.31 |
| capsule cured at 65° C. | 3.3 | 12.3 | 1.32 | 4.73 |
| capsule cured at 75° C. | 3.8 | 11.4 | 1.52 | 4.38 |
| capsule cured at 80° C. | 3.2 | 10.5 | 1.28 | 4.03 |

It is quite clear that the polyurea fragrance capsules cured at 55° C. has better long term sensory performance than capsules that were cured. This can be quite important for fragrance delivery as the degree of undesirable side reaction can be minimized at lower temperature leading to better hedonics for fragrance delivery Example 14

Demonstration of the Effect of Curing Temperature on the Level of Residual Isocyanate level This example demonstrates that the amount of residual isocyanate can be reduced by increasing the curing temperature. This will facilitate the use of capsules in some consumer application.

To conduct the experiments, two batches of capsules were prepared using the procedures outlined in example 4 and the capsules were cured at 55° C. and 75° C. respectively. The slurry was then analyzed for residual isocyanate (methylene biphenyl diisocyanate, MDI) which is present in the original Lupranante®M20 using GC-MS. The sample cured at 55° C. were found to have a MDI level of 548 ppm and the sample that were cured at 75° C. were found to have an residual MDI of 110 ppm. This represents a reduction of 400%.

Example 15

Demonstration of the Effect of Shearing Rate on the Level of Residual Isocyanate Level This example demonstrates that the amount of residual isocyanate can be reduced by increasing the shear rate during capsule making. This will facilitate the use of capsules in some consumer application.

To conduct the experiments, two batches of capsules were prepared using the procedures outlined in example 4 and the capsules were cured at 55 for two hours. Batch no. 1 was prepared using a shear rate of 9500 rpm (Ultra Turrax®, T25 Basic, IKA® WERKE) and batch no. 2 was prepared using a shear rate of 13500 rpm. The slurry was then analyzed for residual isocyanate which is present in the original. Lupranante®M20 using GC-MS. The sample prepared at 9500 rpm were found to have a MDI level of 548 ppm and the sample prepared at 13500 was found to have an residual MDI of 380 ppm. This represents a reduction of over 30%.

Example 16

Demonstration of the Effect of Adding Excess Amount of Polyamine on Reducing the Level of Isocyanate This example demonstrates that the amount of MDI could effectively be reduced by adding excess amount of polyamine as requires by the reaction stoichiometry. This will allow the use of capsules in some consumer applications.

To conduct the experiments, two batches of capsules were prepared using the procedures outlined in example 3 and the capsules were cured at 55 C for two hours. Both batch no. 1 and no. 2 were prepared using a shear rate of 13500 rpm (Ultra Turrax®, T25 Basic, IKA® WERKE. The amount of Luprante M20 used was 9.2 g in batch no. 1 with stoichiometric amount of HMDA, 10.8 g (40%) added. The amount of HMDA was increased to 16.2 g (1.5 times that required by stoichiometry) for batch no. 2. The slurry was then analyzed for residual isocyanate which is present in the original Lupranante® M20 using GC-MS. Batch no. 1 was found to have a MDI level of 386 ppm and batch no. 2 was found to have an residual MDI of 263 ppm. This represents a reduction of over 30%. It is expected that the residual amount of MDI can further be reduced by adding more HMDA or polyamine.

Example 17

Demonstration of the Synergistic Effect of Blending Two Polymeric Dispersants Leading to Reduced Viscosity at Elevated Temperature One of the key physical characteristic of a suspension such as capsule slurry is its viscosity. For the capsule slurry to be usable, it has to be flowable. We have found a combination of dispersants that gave rise to excellent rheology profile of the capsules slurry.

To illustrate the synergistic benefits of blending two dispersant, two capsules slurry were prepared using the procedure outlined in example 4, but the curing temperature was increased to 90° C. In sample one, the capsule slurry contained 0.5% Morwet D-425, and in sample two, the capsule slurry contained a mixture of 0.5% Morwet D-425 and 1.5% polyvinyl alcohol PVA, Mowiol 3-83 (Air Products, Allentown, Pa., USA). The use of PVA or D-425 alone gave rise to unacceptable viscosity at elevated temperature such as 90° C.

When the samples were heated to 90° C., samples no. 1 became quite viscous while sample no. 2 remained highly flowable. After the samples were cooled to room temperature, their viscosities were measures with no. 3 spindle at 30 rpm at 23° C. using a Brookfield, DV-III ULTRA Programmable Rheometer (Middleboro, Mass., USA). The viscosity of sample no. 1 was found to be 986 cp while that of sample no. 2 was measured to be 17 cp. The results clearly demonstrated that the synergistic use of Morwet D-425 and Mowiol 3-83 can lead to the preparation of slurry with excellent rheology profile and greatly facilitate its use.

Example 18

Demonstration of the Application Benefit of Polyurea Capsule in Household Application Such as Hard Surface Cleaners This example will illustrate the performance and consumer benefits of polyurea capsules in household applications. Four samples with different wall levels were prepared for evaluation and the formulas are given in Table 6. All capsules were cured at 55° C. The commercial fragrance, Fancy Lavender (International Flavors & Fragrances, Union Beach, N.J.) was used throughout the experiments. All the polyurea capsules were prepared according the procedures outlined in example 4. Since the application of aminoplast capsule were previously discussed in patent literature for hard surface cleaning application. An aminoplast capsule was also prepared for comparative purpose at about 4% polymer wall level. It should be noted that aminoplast capsules with less wall polymer levels could not be prepared because of the limitation of the formulation using aminoplast polymers.

TABLE 6

Formulation of polyurea capsules for hard surface applications

| Samples | Wall polymer level (% of total capsules suspension) | Particle size (micron) |
|---|---|---|
| Aminoplast capsules | 4 | 8.6 |
| Polyurea capsule-1 W | 4.2 | 6.5 |
| Polyurea capsule-0.5 W | 2.1 | 7.2 |
| Polyurea capsule-0.3 W | 1.3 | 6.6 |

To conduct the evaluation, the capsule slurry was mixed in a model hard surface cleaner base which typically contains about 10% nonionic and cationic surfactant. The pH of the formulation is about 7. The fragrance capsule was dosed at 0.45% neat fragrance equivalent to give a concentrate which is further diluted to 10%. Sensory evaluation was done on clean ceramic tiles obtained from local Home Depot. The dimension of the tile is 12"×12". There was 0.5 gram of diluted product applied to each tile and tile was kept in a closed box for evaluation at given time period. The fragrance intensity was evaluated at fresh, 3 hours, and 5 hours before the tile surface were perturbed by sweeping with a broom at different time period by a group of 25 trained panelists using the LMS scale. The results are given in table 7.

TABLE 7

Sensory benefits comparisons of aminoplast and polyurea capsules

| Samples | Evaluation time | Fragrance intensity |
|---|---|---|
| Aminoplast capsules | Fresh | 3.0 |
|  | 3 hrs. | 3.1 |
|  | 5 hrs. | 3.2 |
| Polyurea capsule-1 W | Fresh | 2.53 |
|  | 3 hrs. | 4.09 |
|  | 5 hrs. | 4.82 |
| Polyurea capsule-0.5 W | Fresh | 4.97 |
|  | 3 hrs. | 4.98 |
|  | 5 hrs. | 6.5 |
| Polyurea capsule-0.3 W | Fresh | 6.84 |
|  | 3 hrs. | 10.16 |
|  | 5 hrs. | 12.36 |

As it can be clearly seen that the polyurea capsules were able to consistently deliver more fragrance intensity than the corresponding aminoplast capsules. Further more, the fragrance intensity increased as the amount of wall material decreased in the polyurea capsules. The capsule made with less wall polymer was able to deliver the perfumery more efficiently than capsules made with more wall materials with significant consumer benefits. Such observations had never been discussed in the literature.

We also examined the delivery profiles of the capsules after were kept in the box for 24 hrs. Dry tiles were swept, 2 times with hand broom across each tile, 10 minutes before evaluation to create headspace. Panelist evaluated and marked their rating using the LMS scale and the results are given in table 8.

TABLE 8

Sensory benefits comparisons of aminoplast and polyurea capsules after 24 hours

| Samples | Pre-rubbing intensity | Post-rubbing intensity |
|---|---|---|
| Aminoplast capsules | 3.2 | 14.0 |
| Polyurea capsule-1 W | 3.2 | 13.8 |
| Polyurea capsule-0.5 W | 5 | 14.5 |
| Polyurea capsule-0.3 W | 7 | 13 |

The results illustrates that the polyurea capsules were able to deliver the same amount of fragrance intensity as the aminoplast capsules. But it was superior in delivering fragrance where no mechanical perturbation is applied which can be often the case in consumer applications.

Example 20

Demonstration of the Application Benefit of Polyurea Capsule in Household Application by Manipulating the Capsules Size This result will demonstrate the application of polyurea capsule by manipulating the capsule size. Three polyurea capsules were prepared with a wall polymer weight 0.8%. The capsules sizes are, 6.6, 12.0 and 24 microns, respectively. The sample preparation and evaluation were the same as in Example 18 except that six tiles were used for each sample and the samples were kept in larger chamber. These samples were evaluated as fresh samples, 5 hours after application and the results are given in table 9.

TABLE 9

Sensory benefits polyurea capsules with different capsule size

| Samples | Pre-rubbing intensity, fresh | Pre-rubbing intensity, 5 hrs | Post-rubbing intensity, 5 hrs |
|---|---|---|---|
| Polyurea capsule, 24 μm | 3.27 | 3.74 | 9.56 |
| Polyurea capsule, 12.0 μm | 5.41 | 5.79 | 10.09 |
| Polyurea capsule, 6.6 μm | 10.62 | 11.45 | 8.77 |

It is clearly shown that the pre-rubbing intensity increased significantly as the capsule sizes decreased and the polyurea capsules can deliver excellent consumer benefits without and with abrasion.

What is claimed is:

1. A process for the preparation of an encapsulated fragrance comprising the steps of:
    Preparing a fragrance emulsion wherein a fragrance and polyisocyanate is combined to form an oil phase;
    preparing a surfactant solution;
    emulsifying the oil phase into the aqueous phase to form a fragrance emulsion;
    adding hexemethylene diamine to the fragrance emulsion to form a capsule slurry; and
    curing the capsule slurry at a temperature greater than about 85° C.

2. A process for the preparation of an encapsulated fragrance comprising the steps of:

preparing a fragrance emulsion wherein a fragrance and polyisocyanate is combined to form an oil phase;

preparing a surfactant solution;

emulsifying the oil phase into the aqueous phase to form a fragrance emulsion;

adding hexemethylene diamine to the fragrance emulsion to form a capsule slurry; and curing the capsule slurry at a temperature greater than about 95° C.

* * * * *